(12) United States Patent
Asnis et al.

(10) Patent No.: US 11,419,729 B2
(45) Date of Patent: Aug. 23, 2022

(54) CONSTRAINED ACETABULAR LINER

(71) Applicant: Northwell Health, Inc., New Hyde Park, NY (US)

(72) Inventors: Stanley Asnis, Port Washington, NY (US); Todd Goldstein, Albertson, NY (US)

(73) Assignee: Northwell Health, Inc., New Hyde Park, NY (US)

( * ) Notice: Subject to any disclaimer, the term of this patent is extended or adjusted under 35 U.S.C. 154(b) by 52 days.

(21) Appl. No.: 16/903,991

(22) Filed: Jun. 17, 2020

(65) Prior Publication Data

US 2020/0397590 A1    Dec. 24, 2020

Related U.S. Application Data

(60) Provisional application No. 62/864,240, filed on Jun. 20, 2019.

(51) Int. Cl.
*A61F 2/34* (2006.01)
*A61F 2/46* (2006.01)
*A61F 2/36* (2006.01)

(52) U.S. Cl.
CPC .............. *A61F 2/34* (2013.01); *A61F 2/3609* (2013.01); *A61F 2/4609* (2013.01); *A61F 2002/349* (2013.01); *A61F 2002/3654* (2013.01)

(58) Field of Classification Search
CPC ........ A61F 2/34; A61F 2/3662; A61F 2/3609; A61F 2/36; A61F 2002/349; A61F 2002/3493
See application file for complete search history.

(56) References Cited

U.S. PATENT DOCUMENTS 3,829,904 A * 8/1974 Ling .................. A61F 2/30724
                                                         623/22.39
6,129,765 A * 10/2000 Lopez .................... A61F 2/34
                                                         623/22.15
(Continued)

OTHER PUBLICATIONS

Biomet Constrained Acetubular Liner Product Prochure, Biomet Orthopedics, 2008, https://www.zimmerbiomet.com/content/dam/zimmer-biomet/medical-professionals/hip/freedom-constrained-acetabular-liners/freedom-constrained-acetabular-liners-product-brochure.pdf.

(Continued)

*Primary Examiner* — Brian A Dukert
(74) *Attorney, Agent, or Firm* — Wissing Miller LLP

(57) ABSTRACT

There is provided an acetabular cup liner for a total hip replacement (THR) prosthesis comprising an inner surface with a hemispherical portion having a radius of curvature. The hemispherical portion is disposed about a centerline and it intersects a hemisphere plane perpendicular to the centerline so that the intersection of the hemispherical portion and the plane define a circle having a radius equal to the radius of curvature. The liner further comprises a capture portion continuous with the hemispherical portion that has the same radius of curvature as the hemispherical portion and connects with the hemispherical portion at the hemispherical plane along a first arc of the circle on the plane, and extends a first distance out of the plane. The liner further comprises an insertion portion continuous with the hemispherical portion. The insertion region is connected with the hemispherical portion along a second arc of the circle on the plane. The distance from the centerline to the insertion portion is greater than the radius. The cup liner constrains the femoral ball portion of the THR prosthesis. The femoral ball portion is engaged with the liner by orienting the ball at an angle so that the shoulder portion of the ball aligns with the insertion (Continued)

portion, pressing the ball into the liner, and orienting the ball away from the angle.

17 Claims, 17 Drawing Sheets

(56) References Cited

U.S. PATENT DOCUMENTS

| | | |
|---|---|---|
| 6,234,961 B1 | 5/2001 | Gray |
| 7,335,231 B2 | 2/2008 | McLean |
| 7,682,398 B2 | 3/2010 | Croxton |
| 7,927,376 B2 | 4/2011 | Lesinger |
| 8,790,412 B2 | 7/2014 | McLean |
| 11,033,395 B2 * | 6/2021 | Perez .................. A61F 2/32 |
| 2002/0116068 A1 | 8/2002 | McLean |
| 2006/0217815 A1 | 9/2006 | Gibbs |
| 2016/0250027 A1 | 9/2016 | Bal |

OTHER PUBLICATIONS

Weitzler L et al. Corrosion in retrieved metal liners of modular dual mobility systems for THA ORS 2019 Annual Meeting Paper No. 0079.

* cited by examiner

CONSTRAINED ACETABULAR LINER

This application claims priority under 35 U.S.C. § 119 to U.S. Provisional Patent Application No. 62/864,240, filed on Jun. 20, 2019. The disclosure of that application is incorporated herein by reference.

BACKGROUND

Field

The present application relates to acetabular cups and combinations of femoral stem components and acetabular cups for total hip replacement. In particular, the present disclosure relates to an acetabular cup that forms a stable coupling with the femoral ball coupled with a femoral stem that is resistant to dislocation.

Description of the Related Art

Total Hip Replacement (THR) is a common medical procedure to repair damage to a patient's pelvis and/or femur due to trauma or degenerative disease. A prosthetic joint is implanted to replace the patient's natural joint. One side of the THR joint is formed by an acetabular cup lined with a low-friction material. The cup is implanted into a prepared portion of the patient's pelvis. The other side of the joint is formed by a femoral component implanted in the patient's femur. A metal or ceramic ball at the superior end of the femoral component engages with the acetabular cup. The femoral ball rotates within the cup to provide rotational mobility similar to a natural hip joint.

About 310,800 THR procedures were performed in the United States in 2010 and that number continues to grow. Many patients live for decades with a THR prosthesis. Thus, the number of existent THR prostheses is quite large.

On common complication of THR is the dislocation of the femoral ball from the acetabular cup. It is not uncommon for a busy emergency room to see several patients a week with a dislocated THR prosthesis. Treatment generally consists of reducing the dislocation and providing the patient with a brace to wear while the tissue around the prosthesis heals. Occasionally the hip is nonreducible and the patient is admitted for a revision surgical procedure in an operating room setting. An analysis of register data has shown that dislocation of THR prostheses is one of the main reasons for revision surgery. Even for those patients who are successfully reduced and sent home, however, there is still a high incidence of repeated dislocations. In these cases, revision surgery may be required.

In a routine classical THR the liner of the acetabular cup is a simple hemisphere. The ball at the head of the femur component has the same outer diameter as the liner's inner diameter, allowing the ball to be inserted into the cup and to rotate within the cup. In the natural hip, prior to a THR procedure, a section of connective tissue called the "ligamentum teres" attaches the femoral head to the acetabulum to provide a stable, flexible connection that keeps the natural hip joint from dislocating. The ligamentum teres is removed during a THR procedure. Instead of a ligament, the prosthetic THR ball is held in the cup by the patent's musculature. Muscle preserving surgical techniques as well as post-surgical physical therapy to strengthen and tone muscles around the prosthesis help to stabilize the joint. Within a few months following THR surgery, deep scar tissue forms around the ball and acetabulum, creating a pseudo-capsule, further stabilizing the joint.

Several problems may develop in THRs stabilized by the pseudo-capsule and the patient's musculature. With time the pseudo-capsule may stretch, allowing the femoral ball to move away from the acetabulum making the hip less stable so that a minor trauma can cause a dislocation. Muscles may weaken due to other medical conditions and as the patient ages. Even with a very stable THR, a fall or accident can cause dislocation. Once dislocation happens, the pseudo-capsule may be torn. In some cases, this may lead to a defect in the capsule that does not close. The defect makes repeated dislocation very common. There are also anatomic variations in many patients that make the classic THR stabilized by the patient's tissues more prone to dislocation.

One way to address these dislocations is by implanting a "Constrained THR" prosthesis either during the initial THR procedure when the natural joint is replaced or during revision surgery. A constrained THR provides a mechanism to mechanically lock the femoral ball into the acetabular liner. There are several types of constrained THR prostheses currently available, but these designs have shortcomings.

One known type of constrained THR prosthesis is called a Dual Mobility System. A metal acetabular cup is implanted in the patient's hip and a polished metal liner is provided within the acetabular cup. A plastic head fits inside metal liner and is mechanically retained so that it can rotate with respect to the cup. A ceramic or metal ball at the head of the femoral component snaps into the plastic head and is held in the head by an interference fit.

Several problems are associated with dual mobility THR prostheses. Since the acetabular shell and the liner are both metallic, cyclical loading of the joint may lead to spalling, fretting, corrosion, and erosion of the metal surfaces. The joint may fail as a result of wearing down of these surfaces. In addition, the worn metal surfaces may release of metal ions into the surrounding tissue. Also, to accommodate the metal liner and plastic head, the inner metal or ceramic ball at the head of the femur is small, reducing the surface area over which cyclical loading is distributed. This may cause increased wear, potentially causing the joint to fail.

Another type of known constrained THR uses a fenestrated plastic liner retained in the acetabular cup. The fenestrations allow the opening of the cup to flex open so that the femoral ball can be forced into the cup. The ball is then constrained by the cup, which flexes inward. Once the femoral ball is inside the cup a metal ring is fitted around the fenestrated portion to prevent the opening of the cup to flex, locking the ball within the cup. Fenestrations in the liner can lead to areas of stress concentration, which may lead to fatigue and breakage when the prosthesis is subjected to cyclical loading caused by the patient's body movement. In addition, because additional liner material and a retaining ring need to be provided around the opening to the liner, this type of constrained THR may provide a reduced range of motion.

Another type of constrained THR prosthesis is sold by Biomet under the tradename "Freedom Constrained Liner System." A polymer acetabular cup is provided with a circular opening. A femoral ball designed specifically to couple with the liner is provided. The ball is connected with the stem of a femoral component during the THR procedure. The ball has a spherical diameter that matches the inner spherical surface of the liner, except that reduced diameter equatorial ring is provide around the ball. The diameter of the equatorial ring is sized to fit into the liner opening, which is smaller than the diameter of the ball by about 1 mm. To couple the ball with the liner, the ball is positioned with the equatorial ring coplanar with the liner opening and the ball is forced into the liner. When the ball rotates away from the orientation where the equatorial ring and opening are aligned, the ball is constrained within the liner. A problem with this design is that a relatively small overlap of the liner and ball is provided to constrain the ball in the liner. In addition, the acetabular cup liner of this THR can be used only with the specific femoral ball including the incised equatorial ring. The cup liner is not compatible with femoral balls made according to industry standard dimensions. Thus, revision surgeries performed with this THR require replacement of both the acetabular cup and the femoral ball.

Yet another constrained THR prosthesis is described in U.S. Patent Appl. Pub. No. 2016/0250027. This application describes an acetabular liner with a greater-than-hemispheric shaped cavity. Slots are provided that allow a femoral ball to be inserted into the liner when the ball is positioned so that the shoulder of the ball aligns with the slots. In this orientation, the ball fits into the cavity within the liner. Notably, the ball must be rotated so that the shoulder of the ball is perpendicular to the hemispherical plane of the liner. In this orientation, the ball must be separated from the stem of the femoral component of the THR prosthesis when the ball is coupled with the liner. This arrangement requires assembling the femoral ball onto the stem after it is placed in the acetabular liner and after the femoral component is secured to the patient's femur. Assembly of the ball onto the stem first requires significant force be applied to separate the components enough to fit the stem into the ball. Then the bone of the greater trochanter or proximal shaft must be hit with significant force to securely lock the Morse taper. In addition, where revision surgery is required, an existing femoral ball would need to be separated from the femoral stem before the ball is joined with the cup described in this application and then the ball would need to be rejoined with the stem after coupling the ball and liner.

SUMMARY

The present disclosure relates to apparatuses and methods to address these and other difficulties of known devices. According to one embodiment of the disclosure there is provided an acetabular liner that can alleviate many of the problem of known constrained THR prostheses.

According to another embodiment of the disclosure, there is provided a one-piece liner for a prosthetic acetabular cup made from a low friction material that securely couples with the prosthetic femoral component and resists wear on the cup and the ball of the femoral component. The one-piece liner reduces the complexity of a constrained THR procedure by eliminating the need for separate components to secure the femoral ball.

According to another embodiment of the disclosure, there is provided a prosthetic acetabular cup liner that securely holds the ball of a femoral component without any metal-on-metal contact, preventing spalling, the associated release of metal ions, and other problems associated with metal-on-metal contact.

According to another embodiment of the disclosure, there is provided a liner for a prosthetic acetabular cup that securely holds a femoral ball that does not require fenestrations. This, it avoids introducing stress concentration regions that could lead to fatigue and breakage during cyclic loading.

According to another embodiment of the disclosure, there is provided a constrained THR prosthesis including a femoral component that is engaged with an acetabular cup liner, where the engagement prevents dislocation when the joint is articulated as the patient engages in normal body movements.

According to another embodiment of the disclosure, there is provided an acetabular cup liner for a THR prosthesis that engages with standard femoral components for use in revision surgery to treat patients experiencing THR dislocations using an existing femoral component, thus reducing the complexity of the revision surgical procedure.

According to another embodiment of the disclosure, there is provided an acetabular cup liner that can be joined with a femoral ball while the ball is already engaged with the stem of a femoral component of a THR prosthesis so that the stem does not have to be engaged with a head that is already captured in the acetabular liner.

According to a still further embodiment of the disclosure, there is provided an acetabular cup liner adapted to be fixed to the pelvis of a patient by bone cement, such as polymethylmethacrylate (PMMA) or other medically acceptable grout or adhesive). According to one aspect an acetabular anchor is fixed to the patient's pelvis and then the liner is fixed within the anchor by bone cement disposed between the liner and the anchor. According to another aspect, the acetabular liner is fixed directly to the patient's pelvis by using bone cement without an anchor.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
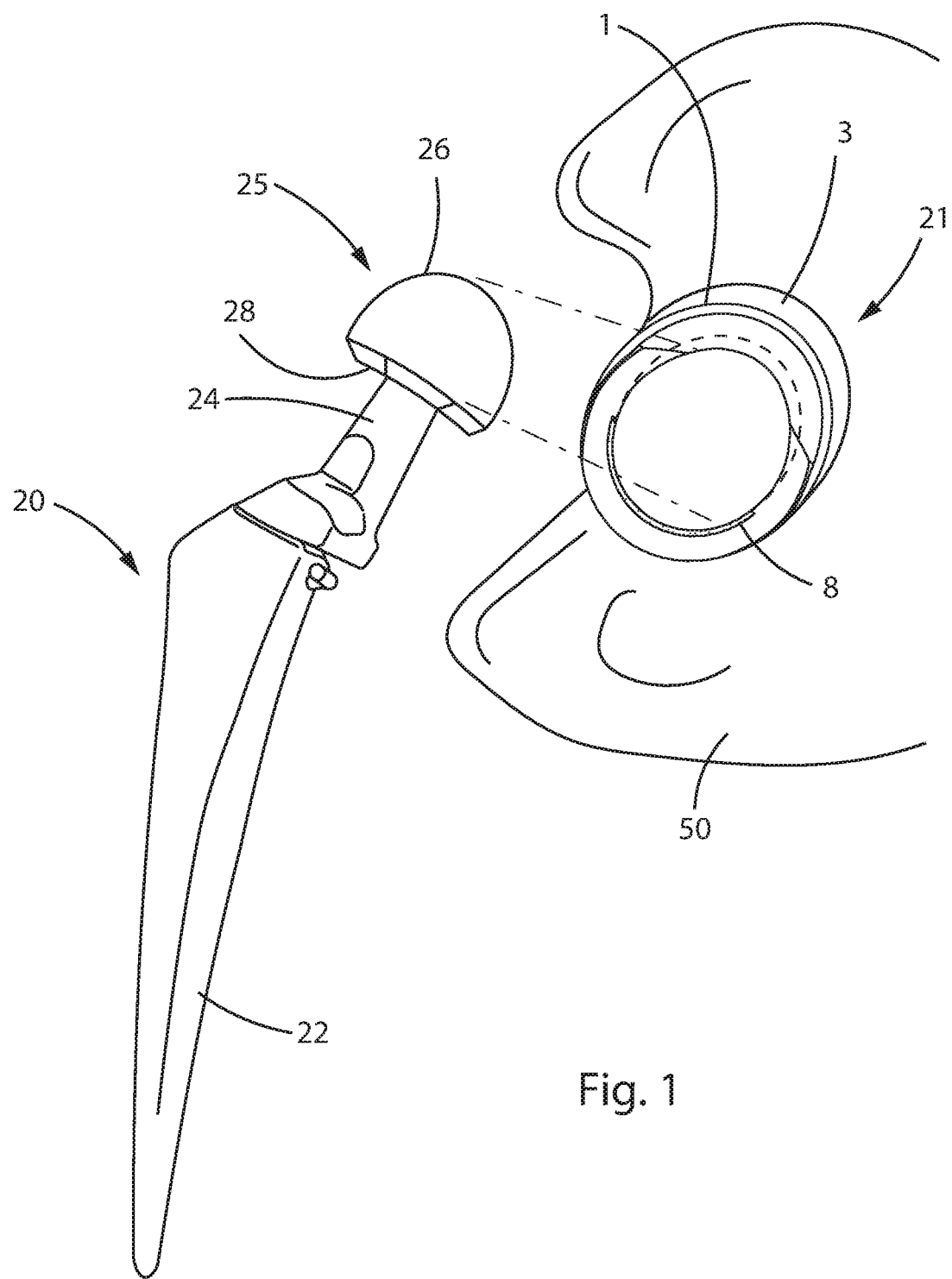
FIG. 1 is an elevation view showing a THR hip prosthesis according to an embodiment of the disclosure.

FIG. 1 is a perspective view of the components of a THR prosthesis according to an embodiment of the disclosure. A femoral component 20 includes a femoral stem 22. At the top of the femoral component 20, that is, the superior end when implanted in a patient, there is a femoral ball 25. The ball has a constant diameter surface 26 that terminates in a planar shoulder 28. Femoral neck 24 connects the femoral ball 25 with the stem 22. According to one embodiment, the constant diameter portion of femoral ball 25 has a diameter of 36 mm. The distance from the planar surface 28 and the farthest extension of surface 26 is 30 mm. These dimensions are provided for purposes of illustration. Other sized femoral components can be used within the scope of the disclosure, provided the appropriate size modifications are made to the acetabular component as will be explained below.

An acetabular cup component 21 couples with the femoral component 20. The cup 21 is formed from an anchor portion 3 that is bonded to the patient's pelvis 50 according to one embodiment of the disclosure, and an acetabular cup liner 1 that is affixed inside the anchor 3. Anchor 3 may comprise a hemispherical metallic shell.

During a THR procedure, the patient's femur is prepared by removing the natural head of the femur. The surgeon inserts stem 22 into a prepared cavity inside the femur and secures it using a bone ingrowth surface, bone cement, grout, or other fixation methods known to those of skill in the field of the invention. The patient's pelvis 50 is prepared by enlarging the natural acetabulum, removing the cartilage, and shaping it to a specific inside diameter. The acetabular cup 21 is secured to the prepared pelvis 50, again using methods known to those of skill in the field of the invention. According to one embodiment, the surface of the anchor 3 and stem 22 may be provided with materials or surface characteristics that encourage tissue growth to form a stable connection with the bone.

Figure 2A:
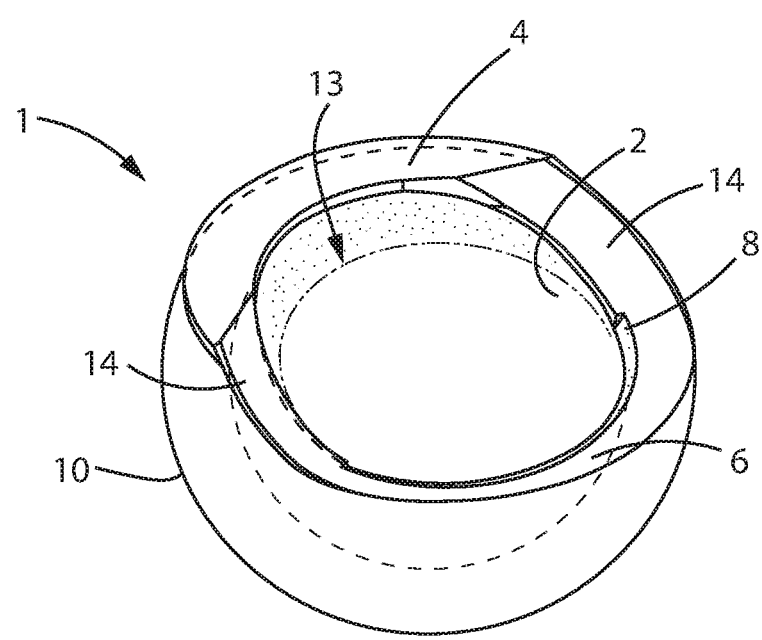
FIGS. 2a-c are perspective, cross-sectional, and top views, respectively, of an acetabular cup liner according to an embodiment of the disclosure.
Figure 2B:
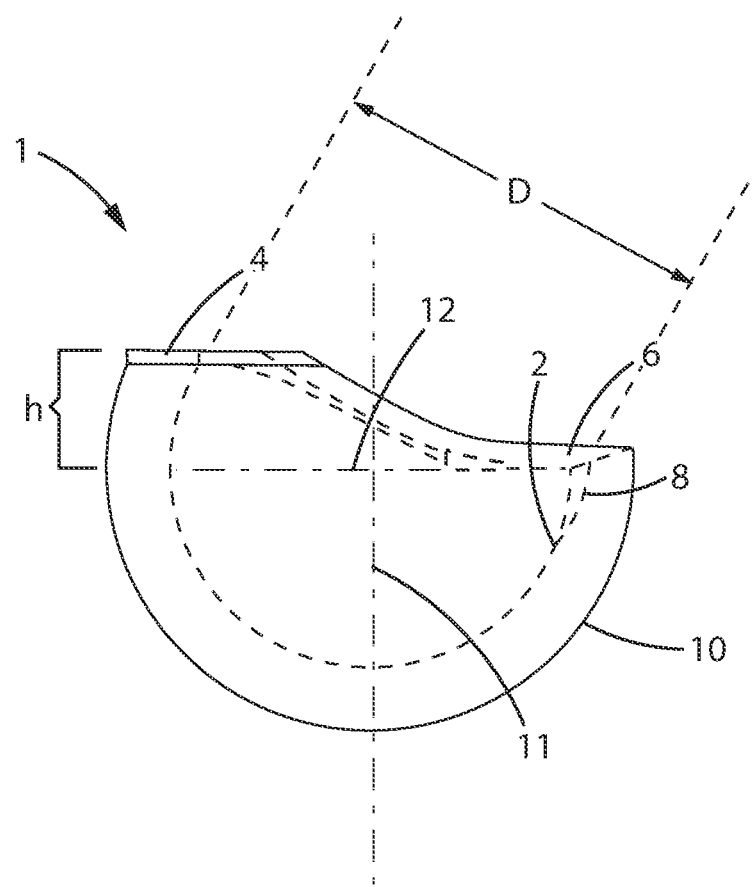
Figure 2C:
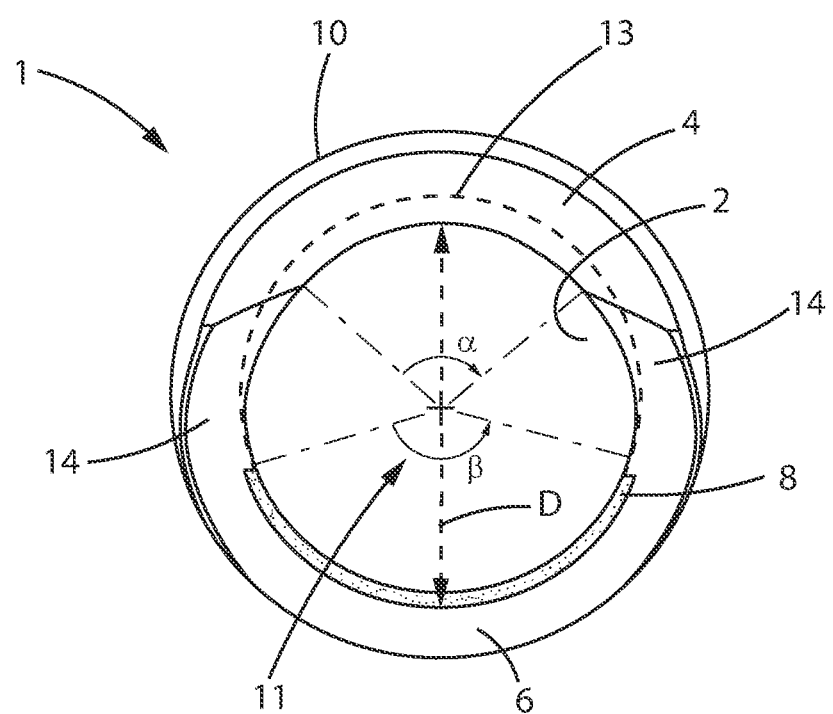

FIGS. 2*a-c* show perspective views of the acetabular cup liner 1 according to an embodiment of the disclosure. For clarity, the acetabular cup liner 1 is shown without the surrounding anchor 3. The liner 1 includes an inner constant diameter surface 2 and an outer surface 10. Outer surface 10 is secured with anchor shell 3 to fix liner 1 to the bone tissue of the patient's pelvis, as shown in FIG. 1. According to an alternative embodiment, liner 1 is fixed directly with the patient's bone tissue without an anchor. The inner surface 2 has a diameter substantially equal to that of constant diameter portion 26 of femoral ball 25. When the ball 25 is installed inside the liner 1, the prosthesis allows the patient's femur to rotate smoothly with respect to the pelvis, thus restoring mobility.

As shown in FIGS. 2*b* and 2*c*, hemispherical plane 12 intersects a hemispherical inner surface 2 with a constant diameter and defines a circle 13 about the central axis 11 of the liner 1. Retaining region 4 joins continuously with surface 2 along a portion of circle 13 with the same radius of curvature on its inner surface as surface 2. Thus, on the inner surface of retaining region 4, constant diameter surface 2 extends past hemispherical plane 12 by a first distance, "h." As a result, the size of the opening, shown in FIGS. 2*b* and 2*c* as the maximum opening distance D from the edge of the retaining region 4 to the edge of the insertion region 6, is reduced from the diameter of the constant diameter surface 26 of ball 25. When ball 25 is engaged with liner 1, retaining region 4 contacts surface 26 of the femoral ball to retain ball 25 in liner 1 and maintain stability of the prosthesis.

According to one embodiment, retaining region 4 extends distance h between about 1 mm and about 10 mm from plane 12. According to a more preferred embodiment, retaining region extends distance h between about 3 mm and about 8 mm and from plane 12. According to a most preferred embodiment, retaining region 4 extends distance h about 4 mm from plane 12.

Retaining region 4 subtends an angular distance a about central axis 11, as shown in FIG. 2*c*. According to a preferred embodiment, retaining region 4 subtends an angle α between 45° and 180° of arc about circle 13. According to a more preferred embodiment, retaining region 4 subtends angular distance a between about 90° and about 150° of arc about circle 13. According to a most preferred embodiment, retaining region 4 subtends angular distance a about 120° of arc about circle 13.

Located along circle 13 diametrically opposite from retaining region 4 is insertion region 6. Insertion region 6 joins continuously with spherical surface 2 along a second portion of circle 13. According to a preferred embodiment, insertion region 6 intersects the hemispherical plane 12 on surface 2. That is, surface 2 does not extend past hemispherical plane 12 in insertion region 6. According to another embodiment, insertion region 6 does extend past hemispherical plane 12 by a distance less than h. According to one embodiment, insertion region 6 subtends an angle β about central axis 11 between 90° and 180° of arc. According to a preferred embodiment, insertion region 6 subtends an angle β of about 130° about axis 11.

As shown in FIGS. 1 and 2*a-c*, insertion region 6 includes an increased radius portion 8. The radial distance between portion 8 and the centerline 11 is larger than the radius of curvature of surface 2. The increased radius provides an opening sufficient to allow ball 25 to enter the liner 1, as will be described below.

According to an embodiment where the maximum distance from plane 28 to the furthest extension of surface 26 of femoral ball 25 is 30 mm, the maximum distance from portion 8 to retaining region 4 is also 30 mm to allow the ball 25 to move smoothly into liner 1. According to another embodiment, the distance between the portion 8 and retaining region 4 is somewhat less than 30 mm to provide an interference fit between the liner 1 and ball 25. Such an interference fit may be advantageous because it provides the surgeon with a tactile "snap-fit" that assures that the ball is fully seated in the liner. Portion 8 may extend along the whole of insertion region 6 or may extend along only a portion of insertion region 6. Portion 8 may be in the form a shoulder relieved into the edge of insertion region 6. According to a more preferred embodiment, as shown in FIG. 2*b*, portion 8 forms a smooth transition with surface 2.

According to one embodiment, transition regions 14 are provided along circle 13 between the retaining region 4 and the insertion region 6 to provide a smooth surface along the face of liner 1. According to one embodiment, the inside surfaces of the transition regions 14 is also continuous with the constant diameter surface 2 and has the same radius of curvature as surface 2. Since the transition regions 14 extend beyond the hemispherical plane 12, the transition regions provide additional area to hold ball 25 captive in the cup liner 1. According to one embodiment, the transition regions 14 are continuous with the retaining region 4 at a first end and with the insertion region 6 at a second end. According to a further embodiment, the distance the transition regions extend out of the hemispherical plane 12 varies continuously along the arc subtended by the transition regions 14 along circle 13. According to a further embodiment, the distance the transition regions extend out of the hemispherical plane 12 varies as a linear function of angle of arc subtended by the transition regions 14 along circle 13.

Figure 5A:
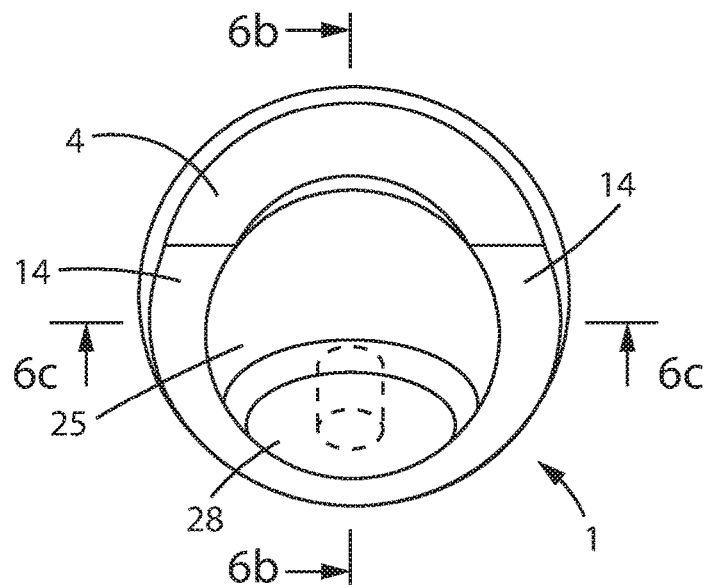
FIG. 5a-c show a perspective and cross-sectional views of a femoral ball engaging with an acetabular cup liner according to an embodiment of the disclosure.
Figure 5B:
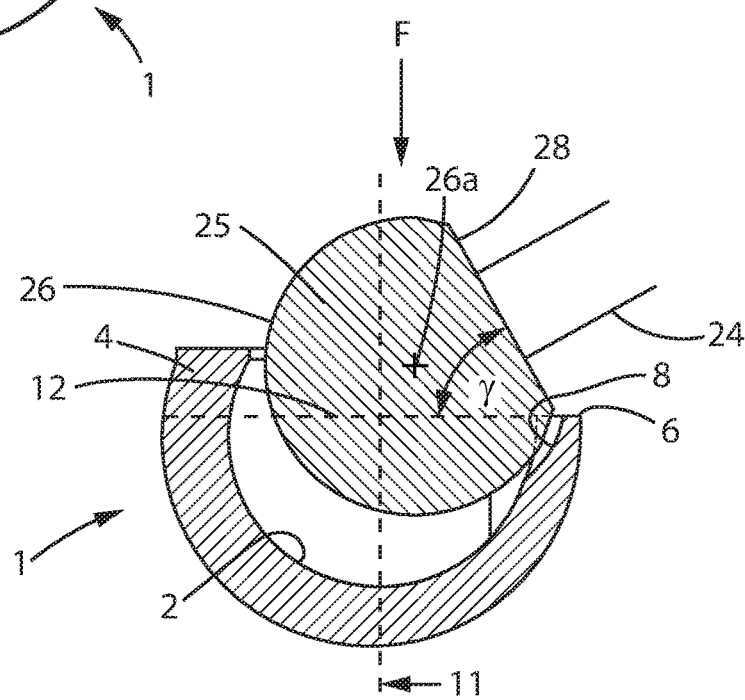
Figure 5C:
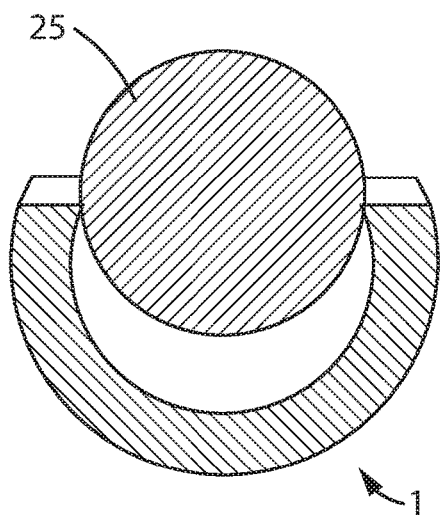

FIGS. 5*a-c* show a femoral ball 25 being inserted into a liner 1 according to an embodiment of the disclosure. According to one embodiment, the ball 25 is joined with neck 24 of femoral component 20 before ball 25 is inserted into liner 1. This embodiment may be advantageous because ball 25 can be impacted onto neck 24 outside of the surgical field. Also, for revision surgeries, an existing femoral component including ball 25 is already in place in the patient's femur when the acetabular cup is fixed to the patient's pelvis. A device according to this embodiment allows the surgeon to leave the existing femoral component intact, potentially reducing the complexity of the procedure. According to an alternative embodiment, ball 25 is joined with liner 1 first, before femoral portion 22 is joined with ball 25.

As shown in FIGS. 5a and 5b, ball 25 is positioned so that planar shoulder 28 is at an angle, γ, with respect to the hemispherical plane 12. As shown in FIG. 5b, femoral neck 24 is at an oblique angle with respect to the edge of insertion region 6. Because neck 24 is tilted away from the edge of the liner 1, the neck will not interfere with the insertion of ball 25 into liner 1. Thus, a prosthesis according to embodiments of the disclosure allows a femoral component 20 to be joined with an acetabular cup assembly 21 while the femoral component is fully assembled. Spherical ball surface 26 of the ball contacts the edges of retaining region 4 and transition regions 14 of the liner. An edge of planar shoulder 28 is within the increase radius portion 8. As shown in the cross section in FIG. 5b, ball center 26a of constant diameter surface 26 is displaced from the centerline 11 of liner 1. Angle γ is referred to herein as the "insertion angle."

A force F is applied to ball 25 in the downward direction as shown in FIG. 5b. According to one embodiment, ball 25 moving downward causes transition regions 14 to flex outward slightly. According to another embodiment, the dimensions of the liner and ball are selected so that the ball at the insertion angle moves into the liner without flexing the liner. As ball 25 moves downward into liner 1, it translates to the left in the view shown in FIG. 5b so that spherical surface 26 contacts inside surface 2 of liner 1 and the center 26a of surface 26 aligns with the centerline 11 of liner 1.

Figure 6A:
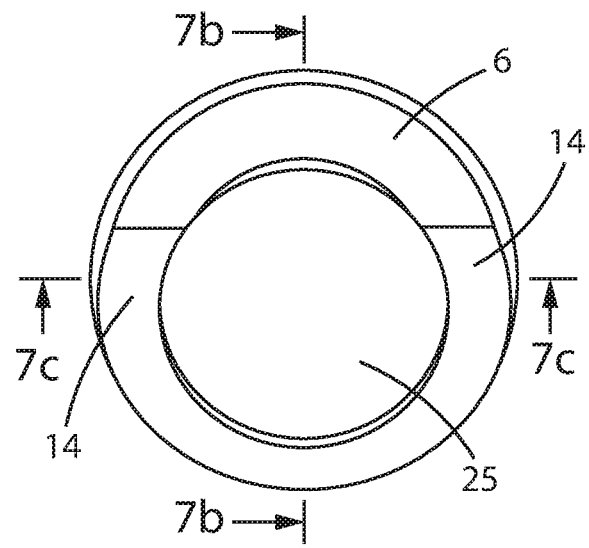
FIGS. 6a-c show a perspective and cross-sectional views of a femoral ball fully engaged with an acetabular cup liner according to an embodiment of the disclosure.
Figure 6B:
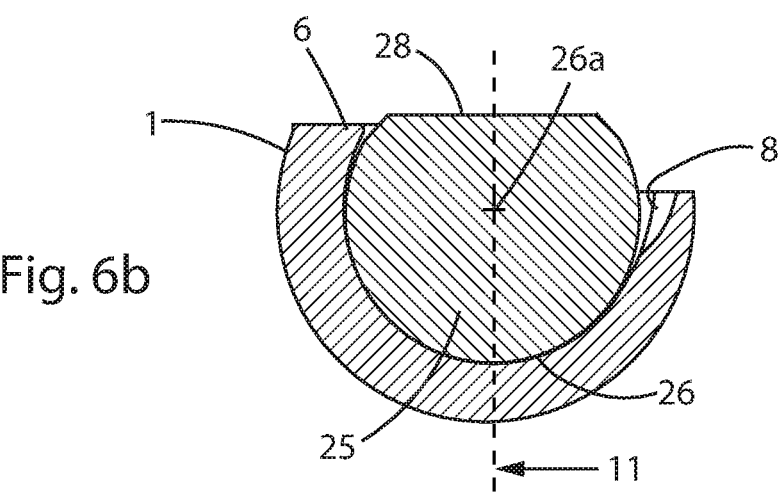
Figure 6C:
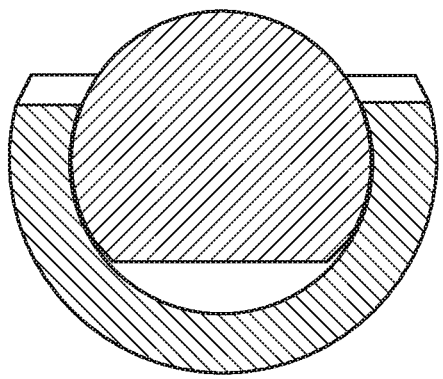

FIGS. 6a-c show ball 25 fully seated inside cup liner 1. For clarity, neck 24 of femoral portion 22 is not shown connected with ball 25. According to alternative embodiments, femoral component 22 may or may not be connected with ball 25 before ball 25 is inserted into liner 1. Ball 25 is rotated away from the insertion angle so that planar portion 28 is no longer aligned with increased radius portion 8. As a result, ball 25 is constrained within liner 1 and will not exit the liner unless it is again set at the insertion angle and a force (upward in the orientation shown in FIG. 5b) is applied.

Notably, the insertion angle, γ, between the hemispherical plane 12 of liner 1 and planar surface 28 of ball 25 may be selected so that the femoral neck 24, which engages with the ball substantially perpendicular to surface 28, does not interfere with the edge of the liner. This allows the surgeon to join the acetabular and femoral components of the THR while the ball 25 attached to the femoral component 20.

According to a preferred embodiment insertion angle γ is between about 30° and 90°, According to a more preferred embodiment, angle γ is between about 45° and 80°. According to a most preferred embodiment, angle γ is about 60°.

By allowing the ball 25 and liner 1 to be joined after the ball and stem are coupled, several advantages are achieved. In most THR prostheses, the ball 25 and stem 22 are connected by providing a Morse taper between them. The ball is secured with the stem by applying impacting blows between the ball and stem. For original surgeries (i.e., not revision surgeries) using an embodiment of the present disclosure, the surgeon can impact the ball onto the stem prior to constraining the ball in the liner. Without this feature, it may be difficult to provide the impact necessary to securely join the ball and stem once the ball and stem are connected because the impact force would have to be applied on the bone of the greater trochanter. Thus, a prosthesis according to the present disclosure may be more convenient and may reduce the size of the surgical incision required. In addition, where a revision surgery is performed to replace the acetabular cup portion of a THR, as will be explained below, the ball 25 of an existing femoral implant can remain in place on the femoral component, thus eliminating the need to separate and then reattach the ball for a revision surgery.

Figure 4A:
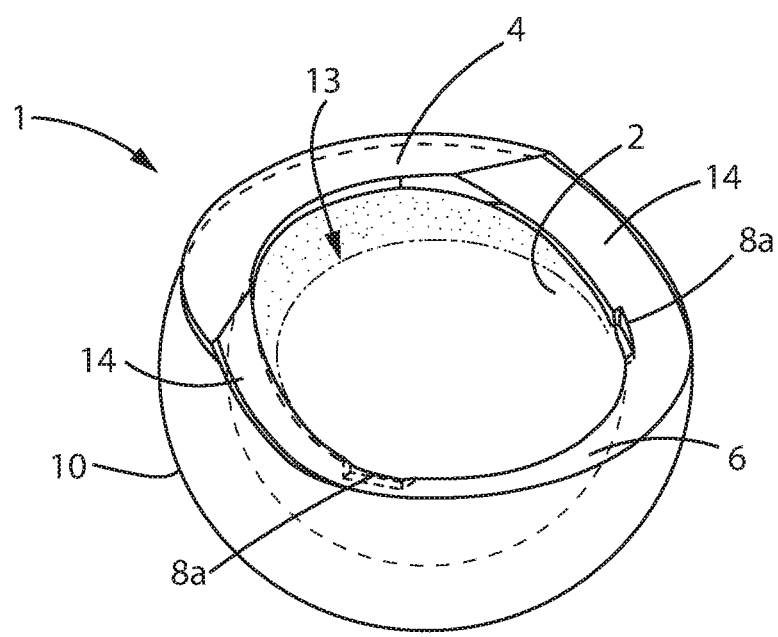
FIGS. 4a-c are perspective, cross-sectional, and top views, respectively, of an acetabular cup liner according to another embodiment of the disclosure.
Figure 4B:
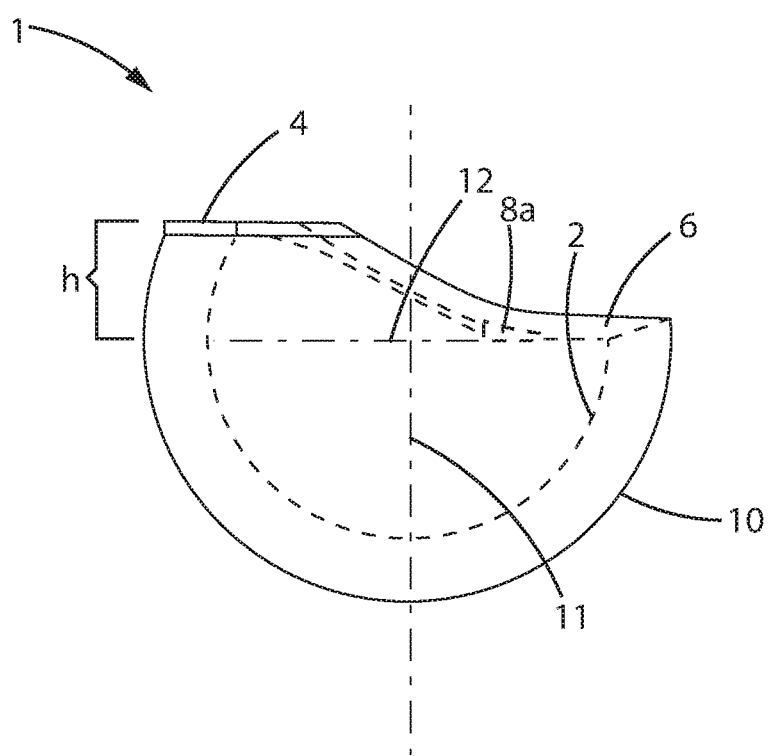
Figure 4C:
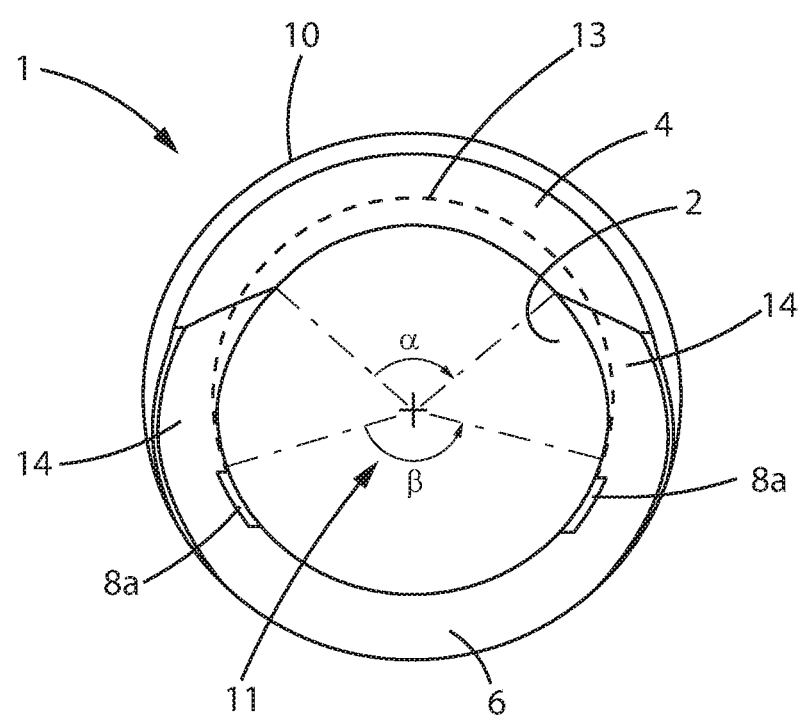

According to one embodiment shown in FIGS. 4a-c, instead of a continuous increased radius portion 8, grooves 8a are formed into surface 2 in insertion region 6. The grooves are positioned symmetrically with respect to the point diametrically opposite retaining region 4 along circle 13. The position, size, and direction of the grooves is selected so that, when femoral ball 25 is positioned at the insertion angle, the constant diameter surface 26 lies along the edge of retaining region 4 and the stem 22 is angled away from the edge of the liner 1. Insertion of the ball into the liner takes place in the same manner described above with respect to FIGS. 5a-c and 6a-c.

When the femoral portion is rotated away from insertion angle γ, shoulder 28 is no longer aligned with portion 8, or with grooves 8a. Femoral ball 25 is now captive inside of surface 2, held within liner 1 by the retaining region 4 and transition regions 14. Because retaining region 4 extends past the hemispherical plane 12, ball 26 cannot exit liner 1. Only by orienting the femoral component 22 so that the ball is again oriented at the insertion angle, γ can the ball 25 and liner 1 be separated.

According to one embodiment, liner 1 is formed as a continuous body with smooth transitions between each of its surfaces. By providing a smooth surfaced body, liner 1 reduces or eliminates stress concentrations that occur, for example, with prior art acetabular cups including fenestrations.

According to a further embodiment of the disclosure, the thickness of liner 1 between inside surface 2 and outer surface 10 is not uniform. Instead, spherical surface 2 is off center of spherical surface 10. According to one embodiment, a thicker portion of the liner is provided on the superior side of acetabular cup 21. Because cyclical loading when the patient walks will impact the superior inner surface of the liner 1, by providing a greater thickness of material longer life of the prosthesis may be achieved. According to a further embodiment of the disclosure, the thicker portion of the liner is aligned with the retaining region 4. This arrangement provides a larger cross-section, higher strength part of the liner in the retaining region to more securely hold the ball within the liner.

According to one embodiment, during the THR procedure, the acetabular cup component 21 is fixed with the patient's pelvis so that the retaining region 4 is oriented superior and the insertion region is oriented inferior to the central axis 11. According to one embodiment, engagement between liner 1 and anchor 3 may include a cogging arrangement, such as by providing mutually engaging protrusions between the liner and cup that allow the cup and liner to engage in a series of angularly distinct orientations, for example, every 22.5°. This arrangement allows a surgeon to adjust the orientation of the liner 1 with respect to the patient's anatomy after the anchor has been fixed to the pelvis.

Figure 3A:
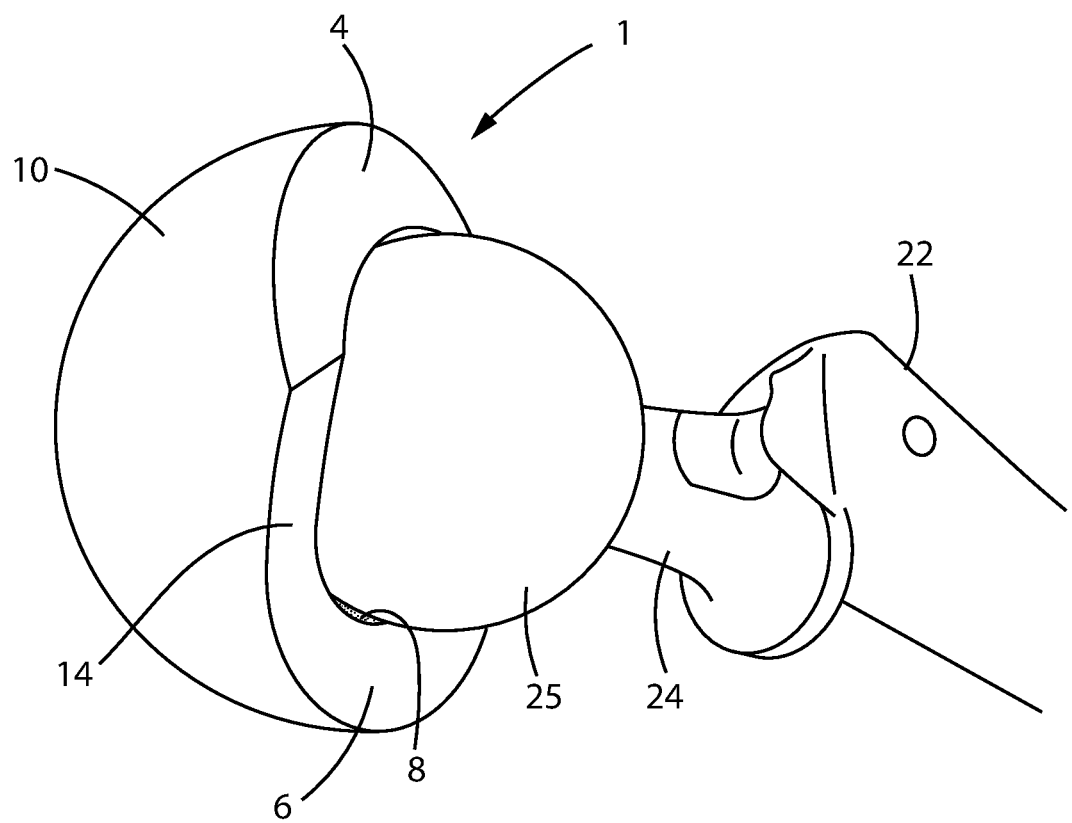
FIGS. 3a-d are perspective views of a femoral component being joined with an acetabular cup according to an embodiment of the disclosure.
Figure 3B:
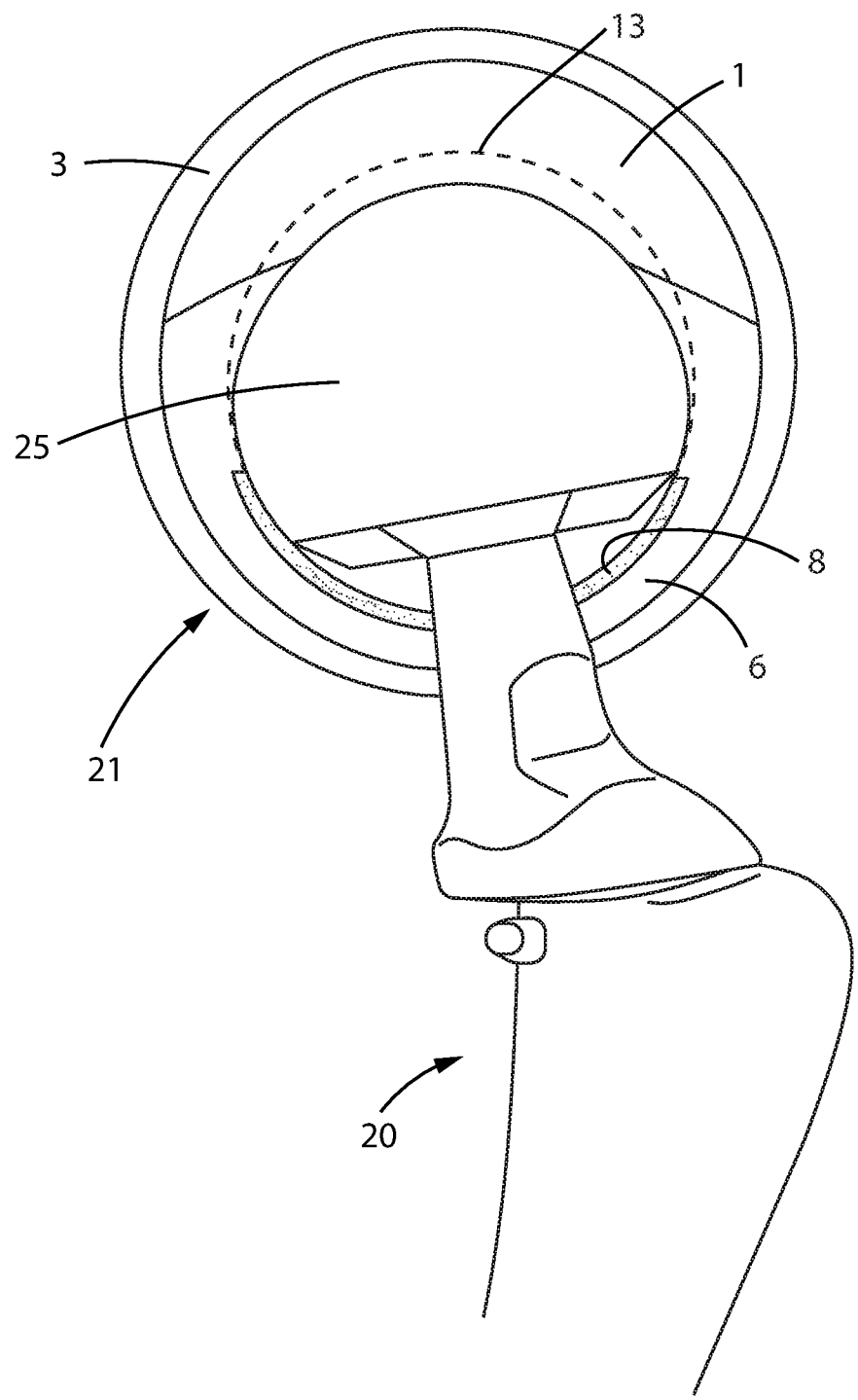
Figure 3C:
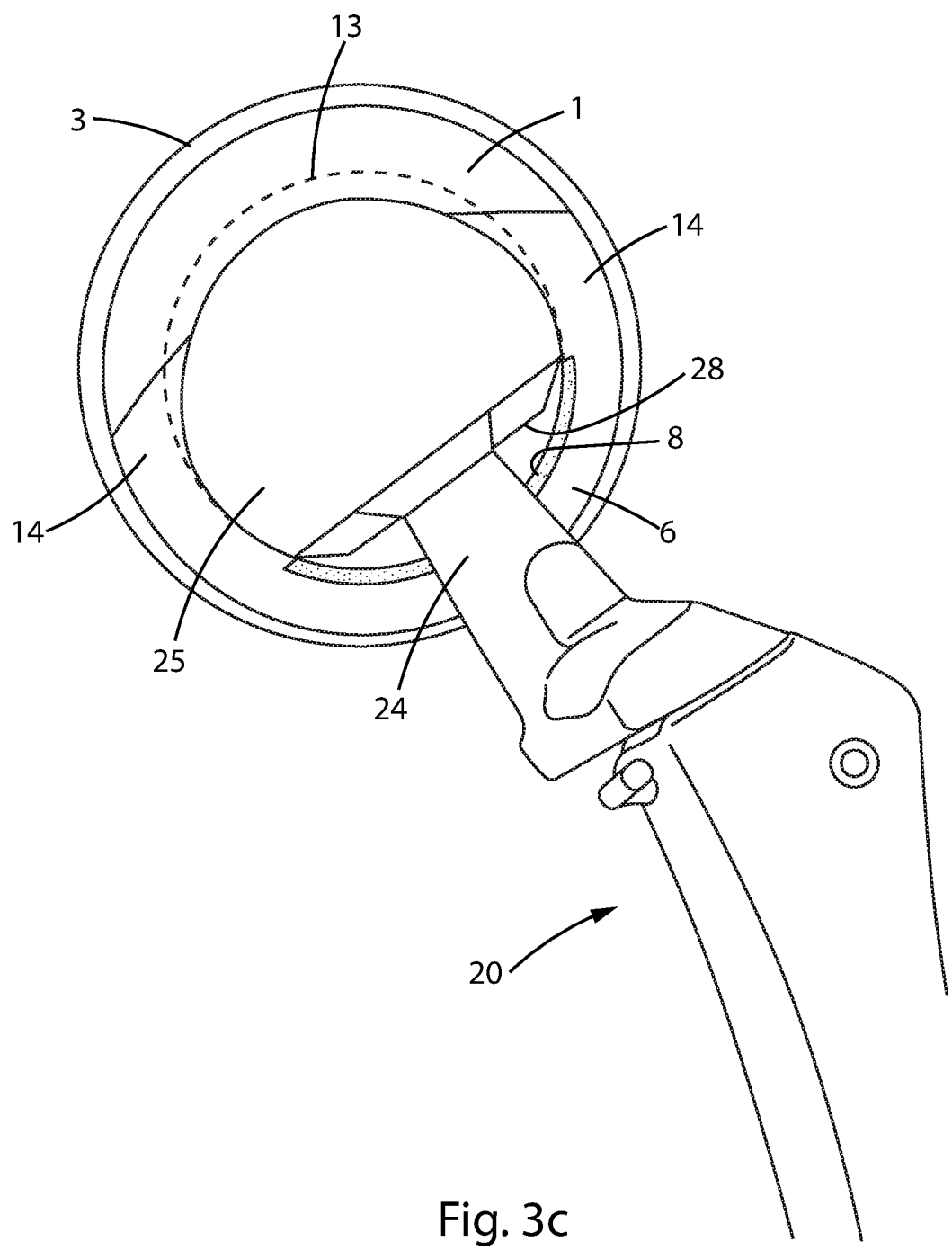
Figure 3D:
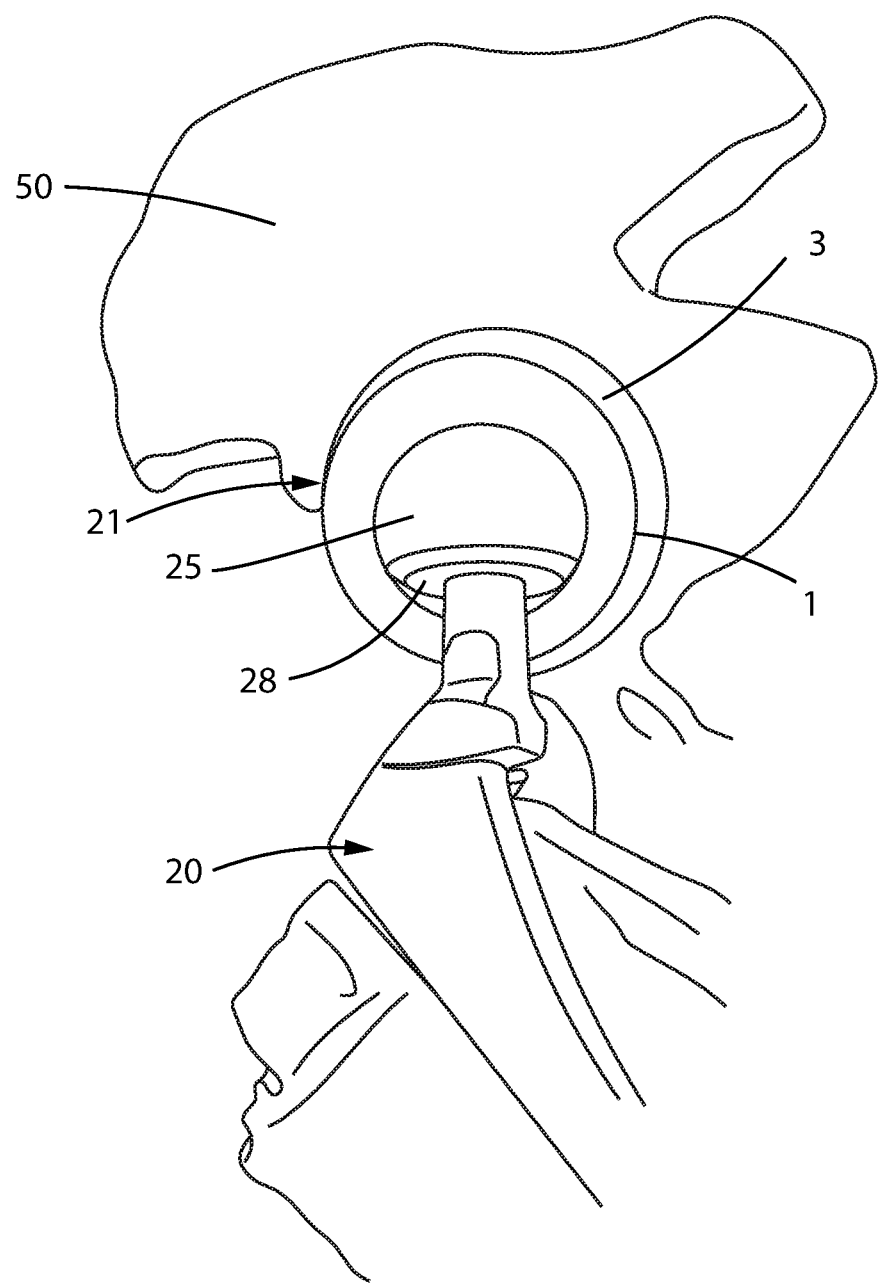

FIGS. 3a-d show steps for insertion of ball 25 of a femoral component 20 into an acetabular cup 21 according to the present disclosure. During the THR procedure, cup 21 is fixed with the patient's pelvis and femoral component 20 is fixed with the patient's femur. Ball 25 is fixed onto neck 24, for example, by mutual engagement of Morse tapered surfaces. As shown in FIG. 3a, ball 25 does not fit into liner 1 when inserted straight on. As shown in FIG. 3b, the patient's leg is moved to orient ball 25 at the insertion angle described above. According to one embodiment, the orientation of cup 21 is selected so that when ball 25 is at the insertion angle, the patient's leg is extended in a position that the patient would not normally assume in daily activities. This assures that the prosthesis will not be put in the insertion angle after the THR procedure. As shown in FIG. 3c, pressure is applied to push ball 25 into liner 1. As described with respect to FIGS. 5a-c and 6a-c, ball 25 translates laterally into the inner cavity of the liner so that surface 26 of the ball contacts inner surface 2 of the liner. As shown in FIG. 3d, the patient's leg is moved so that ball 25 moves away from the insertion angle so that ball 25 is captured within liner 1.

To the extent the prosthesis needs to be separated, for example, during a revision surgery, the femoral component 20 can again be moved so that ball 25 is at the insertion angle and planar surface 28 of ball 25 aligns with insertion region 6. In this orientation, ball 25 can be pulled from the cup liner 1 in a direction opposite of insertion, i.e., upward as shown in FIG. 5b.

The femoral component 20 may be a standard configuration made by a number of manufacturers. Because the size and shape of the femoral ball 25 often follows industry standard practices, an acetabular cup 21 according to embodiments of the disclosure can be used with a variety of femoral components 20 made by different manufacturers. In addition, the length and depth of increased radius portion 8 or grooves 8a may be selected to provide an opening in the liner 1 compatible with a variety of femoral ball configurations, for example, femoral balls with different distances between planar shoulder 28 and maximum extension of the constant diameter surface 26.

An acetabular cup 21 according to embodiments of the disclosure are suitable for a revision surgical procedure, for example, where a patient experiences repeated dislocations with a known prosthetic THR. During such a revision surgery, the patient's femoral prosthesis component is left in place and the femoral ball remains connected with the stem. The patent's acetabular cup prosthesis is removed, and an acetabular cup 21 according to the present disclosure is inserted. The patient's leg is manipulated to put the femoral ball 25 at the insertion angle with respect to the cup liner 1, as described above, and the ball is inserted into the cup liner 1.

Figure 7A:
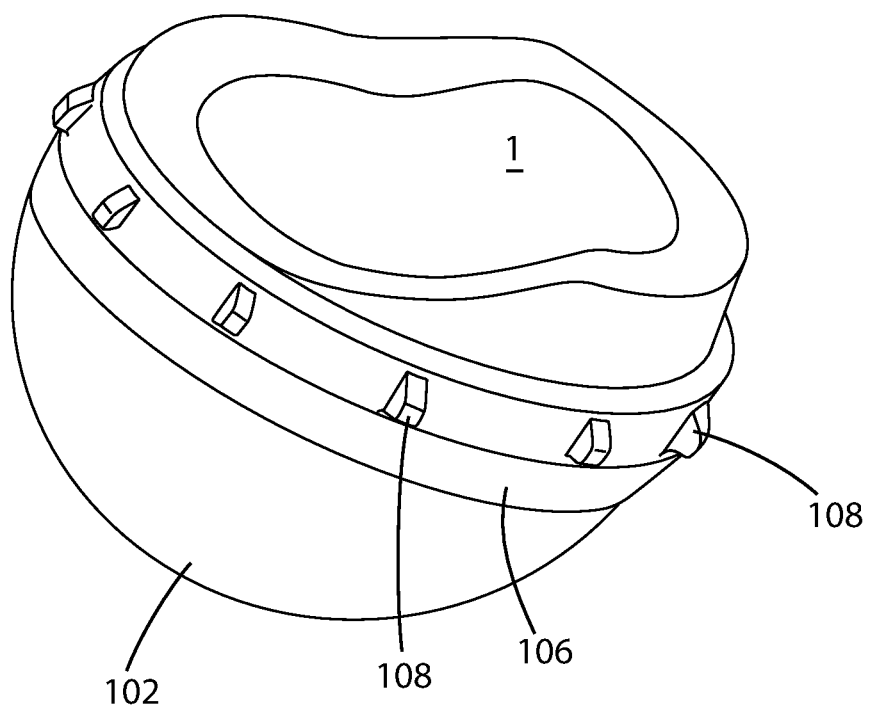
FIGS. 7a-c show perspective and exploded views of an acetabular cup liner according to a further embodiment of the disclosure.
Figure 7B:
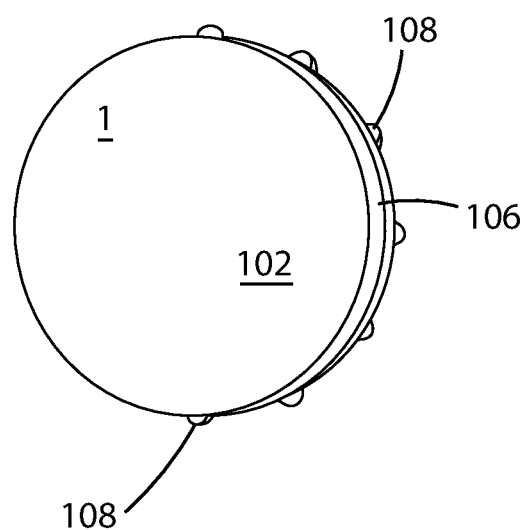
Figure 7C:
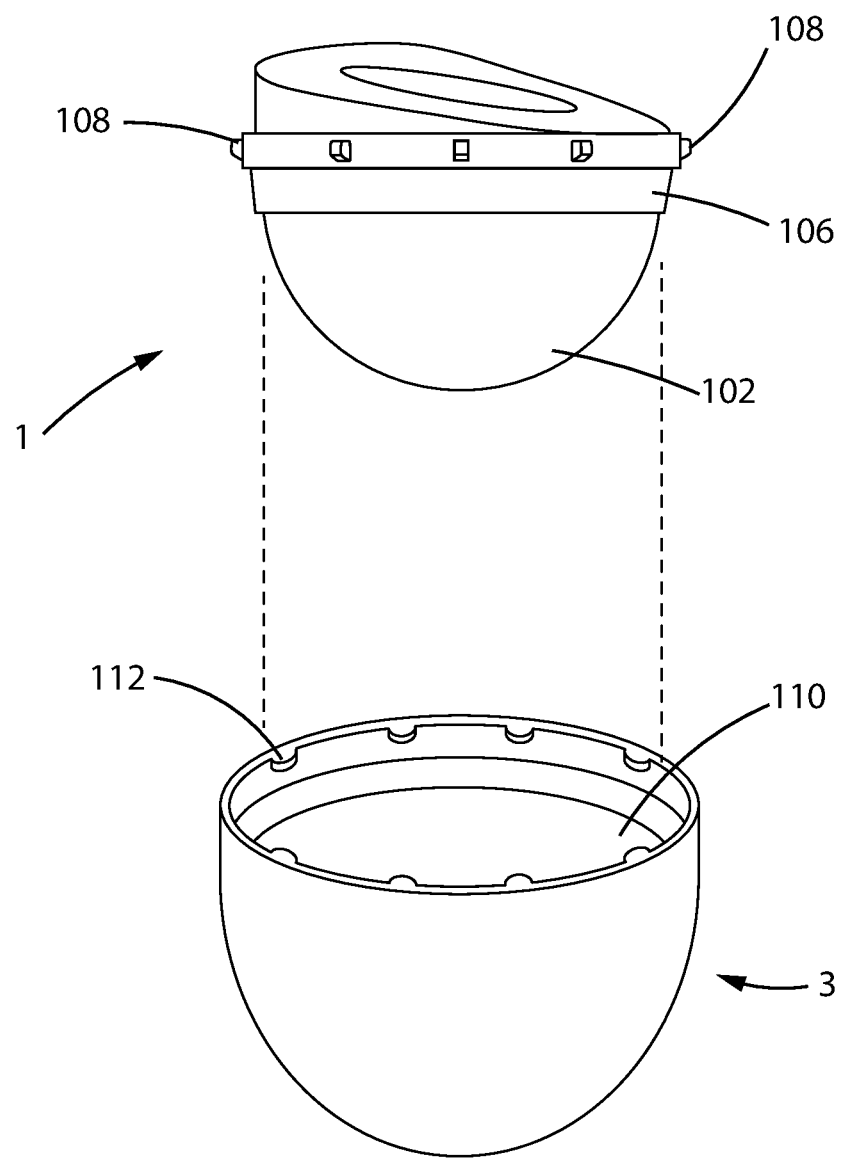

FIGS. 7a, 7b, and 7c show an acetabular cup liner 1 according to a further embodiment of the disclosure. Liner 1 is provided with an outer surface 102 including a coating that facilitates adhesion between the liner and the surface that will receive the liner during the THR procedure. According to the embodiments described with respect to FIG. 1, where liner 1 is received in anchor 3, surface 102 is treated to enhance adhesion to the inner surface of the anchor 3, for example, by providing a chemical bond or an enhanced mechanical bond with a cement placed between the liner 1 and the anchor 3.

According to another embodiment, surface 102 is provided with a coating or treatment that enhances adhesion of liner 1 directly with a patient's tissue. In certain situations, an anchor 3 cannot be implanted during a THR procedure. For example, where the removal of tumors in the bone receiving the acetabular implant has reduced the strength of the bone, it may not be advisable to further thin the bone to accommodate the anchor. Instead, by adhering liner 1 directly to the patient's pelvis, less bone needs to be removed, possibly improving the strength and durability of the hip replacement. Treatment of surface 102 may include providing a surface texture that facilitates penetration of the patient's osteocytes into surface 102.

According to the embodiment of FIGS. 7a-7c, a tapered region 106 is provided about an outer circumference of liner 1. FIG. 7c shows an exploded view of liner 1 that is joined with anchor 3. Anchor 3 includes a tapered region 110 shaped to form an interference fit with tapered region 106 of liner 1. The shapes of regions 106 and 110 are selected to form a secure connection between anchor 3 and liner 1. Various interfering shapes, known to those of skill in the field of the invention, including a Morse taper, or a snap fit connection may be used to create a secure connection. According to one embodiment, liner 1 is secured with anchor 3 by applying an impact, such as by a hammer blow, to securely fix the liner 1 and anchor 3 with one another.

As shown in FIGS. 7a, 7b, and 7c, liner 1 includes protrusions 108 arranged about its peripheral edge. As shown in FIG. 7c, when liner 1 is inserted into anchor 3, protrusions 108 are received into slots 112 formed along an inside surface of anchor 3. Engagement of protrusions 108 and slots 112 assure that the angular orientation of liner 1 and anchor 3 is fixed. Protrusions 108 and slots 12 may be arranged at convenient angular positions to facilitate orienting the prosthesis during THR, for example, at intervals of 22.5°.

Figure 8:
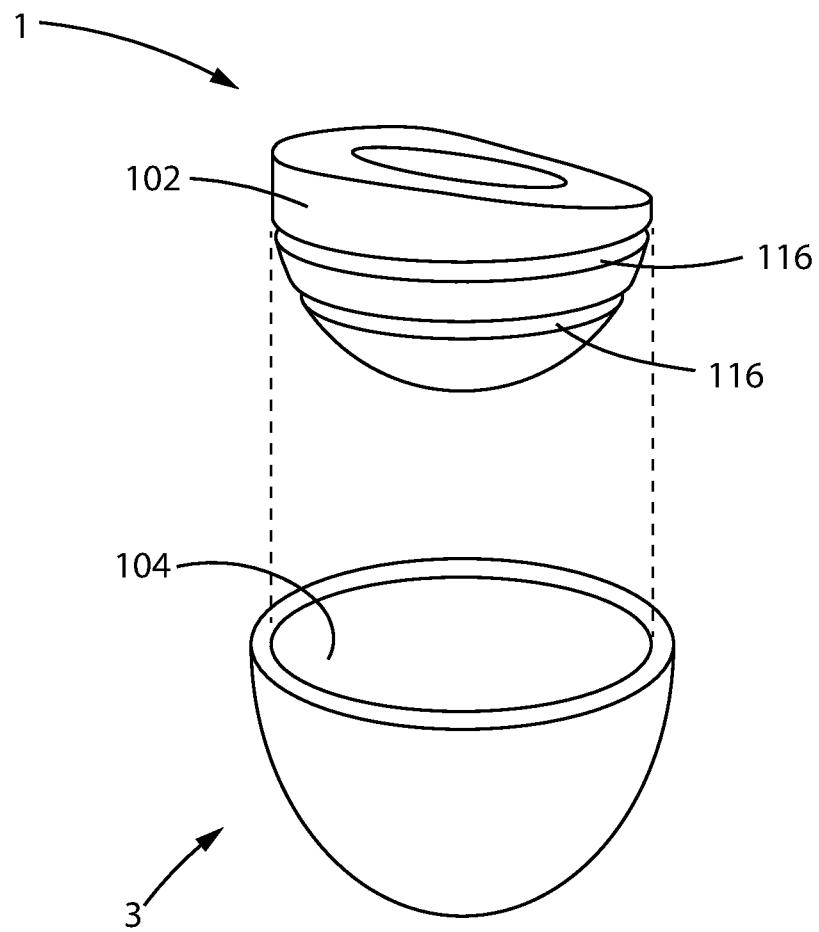
FIG. 8 is an exploded view of an acetabular cup liner and an anchor according to a still further embodiment of the disclosure.

FIG. 8 shows an exploded view of a liner 1 and anchor 3 according to a further embodiment of the disclosure. As with the previously described embodiments, surface 102 may be treated to enhance bonding between the liner and anchor 3 or the patient's bone tissue. According to one embodiment, grooves 116 are provided on the outer surface 102 of liner 1. These grooves further enhance connection of the liner 1 with the patient's pelvis. Grooves 116 provided additional surface area in contact with the cement. Grooves 116 also provided surfaces that are oblique to the surface of the liner 1 so that, when cement solidifies between the liner 1 and the patient's bone tissue, the solidified cement within grooves 116 creates a secure, interlocking connection.

According to one embodiment, liner 1 is formed from a wear resistant material such as a polymer, a ceramic, a metal, and a metal alloy. According to a preferred embodiment, liner 1 is formed from a polymer that provides high wear resistance and good lubricity in contact with the material forming the femoral ball 25, for example, highly crosslinked ultrahigh molecular weight polyethylene. According to one embodiment, the polymer forming liner 1 may be doped with substances that have beneficial effects such as substances that neutralize free radicals, e.g., vitamin E. Other materials known to those of skill in the field may be used to form liner 1 within the scope of the disclosure.

While illustrative embodiments of the disclosure have been described and illustrated above, it should be understood that these are exemplary of the disclosure and are not to be considered as limiting. Additions, deletions, substitutions, and other modifications can be made without departing from the spirit or scope of the disclosure. Accordingly, the disclosure is not to be considered as limited by the foregoing description.

We claim:
1. An acetabular cup comprising a liner having an inner surface, the inner surface comprising:
   a hemispherical surface having a radius of curvature, being disposed about a central axis, and intersecting a hemispherical plane perpendicular to the central axis, the intersection of the hemispherical surface and the plane defining a circle having a circle radius equal to the radius of curvature;

a retaining region continuous with the hemispherical surface, having the radius of curvature, connected with the hemispherical surface at the plane along a first arc of the circle on the plane, and extending a first distance out of the plane;

an insertion region on the hemispherical plane and connected with the hemispherical surface along a second arc of the circle on the plane and comprising an increased radius portion, wherein the hemispherical surface does not extend past hemispherical plane in insertion region, wherein a radial distance from the central axis to the insertion region is greater than the circle radius, and wherein a maximum opening distance from an edge of the retaining region to an edge of the insertion region is less than twice the circle radius.

2. The acetabular cup of claim 1, further comprising a transition region continuous with the hemispherical surface, having the radius of curvature, and extending along a transition arc of the circle between the first arc and the second arc, wherein the transition arc is connected at a first end with the first arc and at a second end with the second arc, wherein, at the first end the transition region extends out of the hemispherical plane the first distance and at the second end the transition region is substantially on the hemispherical plane.

3. The acetabular cup of claim 2, wherein a transition distance the transition portion extends out of the hemisphere plane varies linearly along the transition arc from the first end to the second end.

4. The acetabular cup of claim 1, wherein the increased radius portion comprises a continuous edge concentric with the circle and extending along the second arc.

5. The acetabular cup of claim 1, wherein the increased radius portion comprises two notches disposed along the second arc at equal distances from a diameter of the circle that bisects the retaining region.

6. The acetabular cup of claim 1, wherein the liner extends outward from the hemispherical surface and comprises an outer surface.

7. The acetabular cup of claim 6, further comprising an anchor adapted to be affixed with an acetabulum of an organism, wherein the anchor comprises an inside surface with substantially the same shape as the outer surface of the liner.

8. The acetabular cup of claim 7, wherein the outer surface of the liner comprises one or more grooves.

9. The acetabular cup of claim 7, wherein the outer surface of the liner is affixed to an inner surface of the anchor.

10. The acetabular cup of claim 1, wherein the liner comprises one or more of a polymer, a ceramic, a metal, and a metal alloy.

11. The acetabular cup of claim 7, wherein the anchor comprises one or more of a polymer, a ceramic, a metal, and a metal alloy.

12. A total hip replacement comprising:
a femoral portion comprising,
a femoral stem adapted to be implanted into a prepared femur bone of an organism;
a femoral ball; and
a femoral neck, the femoral neck adapted to connect the femoral ball with the femoral stem,
wherein the femoral ball comprises a spherical ball surface with a ball radius, a ball center at a geometric center of the spherical ball surface, and a planar surface, wherein the femoral neck is adapted to connect with the ball perpendicular to the planar surface, and wherein the planar surface is located an offset distance from the ball center point less than the ball radius, and wherein the offset distance and the ball radius define a ball height equal to the sum of the ball radius and the offset distance; and
an acetabular cup liner with an inner surface, the inner surface comprising:
a hemispherical surface having a cup radius of curvature, being disposed about a cup central axis, and intersecting a hemispherical plane perpendicular to the cup central axis, the intersection of the hemispherical surface and the hemispherical plane defining a circle having a circle radius equal to the cup radius of curvature;
a retaining region continuous with the hemispherical surface, having the same cup radius of curvature, extending along a first arc of the circle on the hemispherical plane, and extending a first distance out of the hemispherical plane; and
an insertion region continuous with the hemispherical surface connected with the hemispherical surface along a second arc of the circle on the hemispherical plane and comprising an increased radius portion, wherein the hemispherical surface does not extend past hemispherical plane in insertion region, wherein a radial distance from the cup central axis to the insertion region is greater than the circle radius,
wherein a cup opening distance is defined by a maximum opening distance between an edge of the retaining region and an edge of the insertion region, and wherein the cup opening distance is substantially the same as the ball height, and wherein the cup opening distance is less than twice the ball radius.

13. The total hip replacement according to claim 12, wherein an engagement between the ball and the liner defines an insertion angle between the neck and the hemispherical plane, and wherein when the ball is at the insertion angle with respect to the liner, the ball can enter the liner.

14. The total hip replacement according to claim 13, wherein the insertion angle is between about 30° and 90°.

15. The total hip replacement according to claim 13, wherein the insertion angle is between about 45° and 80°.

16. The total hip replacement according to claim 12, wherein the insertion angle is about 60°.

17. A prosthesis comprising:
a femoral ball, the femoral ball having a truncated spherical surface defining a spherical surface diameter, a should defining a shoulder plane, and a ball height defined by a maximum distance from the shoulder plane to the spherical surface; and an acetabular cup liner, comprising
an opening, the opening adapted to admit the femoral ball at an oblique insertion angle, and;
a partial spherical inner surface in communication with the opening, the partial spherical surface intersecting a hemispherical plane along a circle, the partial spherical surface extending from the hemisphere plane by a first amount along a first arc of the circle and extending along the hemisphere plane along a second arc of the circle, wherein the partial spherical surface does not extend past hemispherical plane along the second arc, wherein the first and second arcs define a maximum opening distance, and wherein the maximum opening distance forms an interference fit with the ball height, and wherein the maximum opening distance is greater than or equal to the ball height and less than a diameter of the partial spherical surface.

* * * * *